(12) United States Patent
Walker et al.

(10) Patent No.: US 7,429,127 B2
(45) Date of Patent: Sep. 30, 2008

(54) MAGNETOACOUSTIC SENSOR SYSTEM AND ASSOCIATED METHOD FOR SENSING ENVIRONMENTAL CONDITIONS

(75) Inventors: Dwight Sherod Walker, Durham, NC (US); Michael Bernard James, Ware (GB)

(73) Assignee: Glaxo Group Limited, Greenforo, Middlesex (GB)

( * ) Notice: Subject to any disclaimer, the term of this patent is extended or adjusted under 35 U.S.C. 154(b) by 38 days.

(21) Appl. No.: 10/512,268

(22) PCT Filed: Apr. 23, 2003

(86) PCT No.: PCT/US03/12775

§ 371 (c)(1),
(2), (4) Date: Oct. 22, 2004

(87) PCT Pub. No.: WO03/091679

PCT Pub. Date: Nov. 6, 2003

(65) Prior Publication Data
US 2006/0050765 A1   Mar. 9, 2006

(51) Int. Cl.
*G01N 25/02* (2006.01)
*G01K 7/00* (2006.01)

(52) U.S. Cl. .............. 374/109; 374/141; 374/208; 374/16; 374/163

(58) Field of Classification Search .......... 374/16, 374/28, 109, 117–119, 141, 142, 208, 163, 374/21; 73/865.9, 73; 340/604
See application file for complete search history.

(56) References Cited
U.S. PATENT DOCUMENTS

| | | | | |
|---|---|---|---|---|
| 572,322 A | * | 12/1896 | Warner | ......................... 256/35 |
| 3,452,597 A | * | 7/1969 | Grady, Jr. | ..................... 374/117 |
| 3,615,719 A | * | 10/1971 | Michel et al. | .................. 426/88 |
| 4,357,114 A | | 11/1982 | Iwasaki | |
| 4,596,150 A | * | 6/1986 | Kuhr | ............................ 73/779 |
| 4,627,432 A | | 12/1986 | Newell et al. | |
| 4,778,054 A | | 10/1988 | Newell et al. | |
| D299,066 S | | 12/1988 | Newell et al. | |
| 4,811,731 A | | 3/1989 | Newell et al. | |
| 4,850,716 A | * | 7/1989 | Baker et al. | .................. 374/160 |

(Continued)

FOREIGN PATENT DOCUMENTS

EP     0631810 B1    10/1997

OTHER PUBLICATIONS

Remote query measurement of pressure, fluid-flow velocity, and humidity using magnetoelastic thick-film sensors. Article by Grimes et al. Sep. 1999.*

(Continued)

*Primary Examiner*—Gail Verbitsky
(74) *Attorney, Agent, or Firm*—Robert J. Smith

(57) ABSTRACT

A remote sensor system (60) and method for passively sensing environmental conditions, such as temperature and humidity, uses a magnetic impulse from an AC interrogation coil (68) to stimulate a magnetoelastic sensor (62) to generate an acoustic signal (AE) at the resonant frequency of the magnetoelastic sensor (62). The acoustic signal (AE) is received by amplifier (74), detected and displayed (76). The systems and methods are particularly suited for detecting environmental conditions in commercial pharmaceutical packaging, such as blister packs.

17 Claims, 8 Drawing Sheets

U.S. PATENT DOCUMENTS

| | | | |
|---|---|---|---|
| D342,994 S | 1/1994 | Rand et al. | |
| 5,319,975 A | 6/1994 | Pederson et al. | |
| 5,412,372 A * | 5/1995 | Parkhurst et al. | 340/568.1 |
| 5,565,847 A | 10/1996 | Gambino et al. | |
| 5,590,654 A | 1/1997 | Prince | |
| 5,739,416 A | 4/1998 | Hoenk | |
| 5,745,039 A * | 4/1998 | Hof et al. | 340/590 |
| 5,837,630 A | 11/1998 | Owens et al. | |
| 5,860,419 A | 1/1999 | Davies et al. | |
| 5,946,088 A | 8/1999 | Aldridge | |
| 5,997,964 A * | 12/1999 | Klima, Jr. | 428/1.54 |
| 6,025,725 A * | 2/2000 | Gershenfeld et al. | 324/652 |
| 6,032,666 A | 3/2000 | Davies et al. | |
| 6,073,479 A * | 6/2000 | Shapiro et al. | 73/29.01 |
| 6,126,311 A | 10/2000 | Schuh | |
| 6,155,423 A | 12/2000 | Katzner et al. | |
| 6,202,480 B1 | 3/2001 | Mauze et al. | |
| 6,208,253 B1 * | 3/2001 | Fletcher et al. | 340/584 |
| 6,359,444 B1 * | 3/2002 | Grimes | 324/633 |
| 6,393,921 B1 | 5/2002 | Grimes et al. | |
| 6,397,661 B1 | 6/2002 | Grimes et al. | |
| 6,453,749 B1 * | 9/2002 | Petrovic et al. | 73/754 |
| 6,810,350 B2 * | 10/2004 | Blakley | 702/130 |
| 6,839,304 B2 * | 1/2005 | Niemiec et al. | 368/10 |
| 6,999,339 B2 * | 2/2006 | Tuttle et al. | 365/158 |
| 7,004,620 B2 * | 2/2006 | Simunovic et al. | 374/102 |
| 7,089,786 B2 * | 8/2006 | Walker | 73/73 |
| 2003/0051550 A1 * | 3/2003 | Nguyen et al. | 73/514.36 |
| 2004/0113801 A1 * | 6/2004 | Gustafson et al. | 340/604 |

OTHER PUBLICATIONS

Thin-Film Magnetoelastic Microsensors for Remote Query Biomedical Monitoring. Article by Grimes. 1999.*

Grimes, "A remotely interrogatable magnetochemical ph sensor," *IEEE Transactions on Magnetics* 33(5):3412-3414 (Sep. 1997).

Jain et al., "Magnetoacoustic remote query temperature and humidity sensors," *Smart Mater. Struct.* 9:502-510 (2000).

Keat Ghee Ong and Craig A Grimes, "A resonant printed-circuit sensor for remote query monitoring of environmental parameters.", Smart Mater. Struct., 2000, pp. 421-428, vol. 9.

* cited by examiner

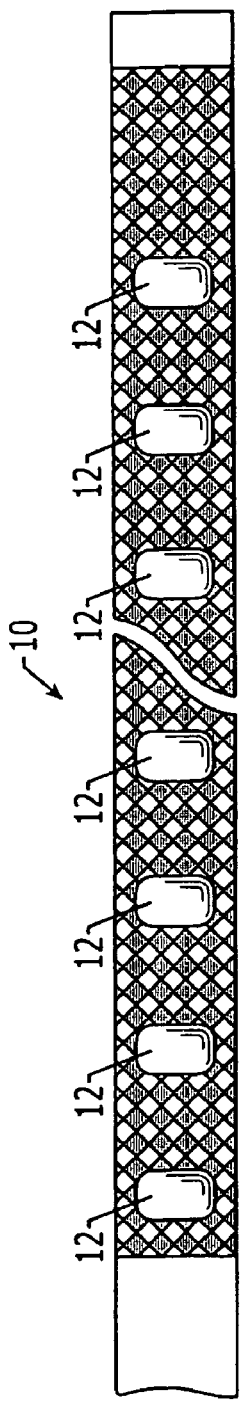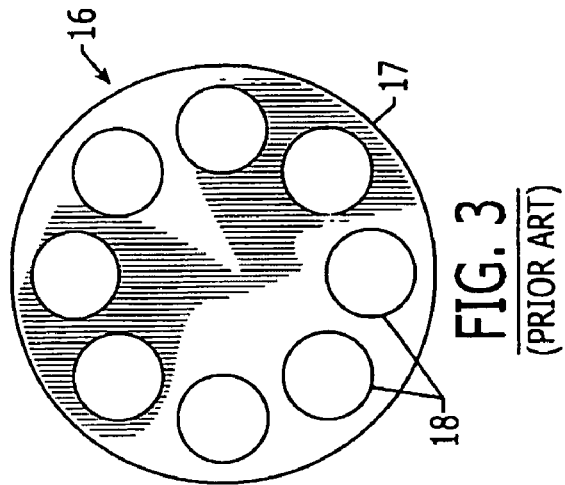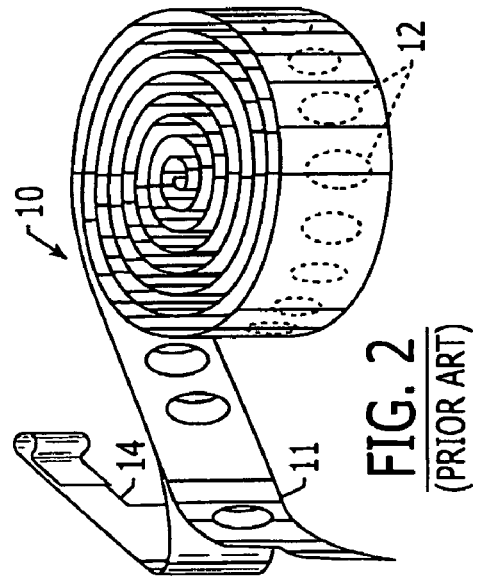

MAGNETOACOUSTIC SENSOR SYSTEM AND ASSOCIATED METHOD FOR SENSING ENVIRONMENTAL CONDITIONS

CROSS-REFENCE TO RELATED APPLICTIONS

This application is filed under 35 U.S.C. § 371 as the United States National Phase Application of International Application No. PCT/US03/1 2775 filed Apr. 23, 2003 claiming priority from U.S. patent application Ser. No. 60/375,522 filed Apr. 25, 2002.

FIELD OF THE INVENTION

The present invention relates generally to devices and systems for sensing environmental conditions. More particularly, the invention relates to a magneto acoustic sensor system and method for sensing environmental conditions, particularly temperature and moisture, and determining values relating thereto.

BACKGROUND OF THE INVENTION

Pharmaceutical packaging, such as sealed pockets, blister strips, disks and packs, for doses of medicaments or pharmaceutical compositions in the form of powders, tablets or capsules are well known in the art. As applied in dry powder inhaler technology, the pharmaceutical packaging (e.g., blister strips) generally comprise a base having cavities, pockets or open "blisters" adapted to receive a pharmaceutical composition (e.g., inhalable dry powder), a lid that encloses the opening of each cavity or blister, and an adhesive or bonding layer disposed there between to effect a seal.

It is further well known that pharmaceutical compositions, and in particular, inhaled dry powders, must be maintained in a hermetic environment to maintain a high degree of physical stability in particle size. Only particles having a specific narrow range of aerodynamic diameter size will deposit in the desired location in the pulmonary system. For instance, a particle for local treatment of respiratory conditions such as asthma will have a particle size of 2-5 µm. Particle to particle agglomeration, shifting the particle size outside of this range, will cause the particle(s) to deposit away from the target region of the lung. Such agglomeration has been associated with moisture ingress into the pharmaceutical packaging (i.e., blister). Particle sizes, either in aerodynamic or geometric measures, referred to herein relate to a particles effective particle size. Effective particle size denotes the apparent particle size of a body without distinction as to the number of individual particles which go to make up that body, i.e., no distinction is made between the single particle of given size and an agglomerate of the same size which is composed of finer individual particles.

Similarly, exposure of a pharmaceutical composition to high temperatures can, and in many instances will, undermine the stability and, hence, efficacy of the pharmaceutical composition. Accordingly, it is important to closely monitor the environmental conditions to which a pharmaceutical composition is exposed to ensure that the pharmaceutical composition's physical and chemical stability has not been degraded.

Various prior art sensors have been employed to monitor environmental conditions proximate a pharmaceutical composition. However, as discussed below, most of the noted sensors are not suitable for use "inside" pharmaceutical packaging, and in particular, blister packs.

For example, surface acoustic wave devices, such as the humidity sensors disclosed by U.S. Pat. No. 5,739,416, require a direct physical connection to the sensor. Since blister packs containing pharmaceutical compositions are sealed, any direct connection to a sensor in an individual blister is impractical. On the other hand, sensors not disposed within the packaging do not necessarily provide an accurate indication of conditions within the interior, particularly with respect to humidity. Further, surface acoustic wave sensors are relatively expensive and, hence, not cost effective for use in commercial applications.

Similar problems exist with conventional temperature sensors. Relatively simple systems employing conventional thermostats as well as more complex systems, such as those disclosed in U.S. Pat. No. 4,357,114 that rely on changing magnetic flux, still require a direct electrical connection to the sensor. As such, these technologies are generally unsuitable for use within sealed pharmaceutical packaging.

Fiber optic and laser telemetry sensors have also been employed to monitor environmental conditions. Illustrative is the fiber optic based moisture sensor disclosed in U.S. Pat. No. 5,319,975. However, this technology requires precise orientation of the sensor as well as a visual connection.

Another method of remote determination of one or more environmental conditions is to monitor the induced resonant vibration of a magneto elastic strip or sensor. A basic example of this technology is in the field of electronic article surveillance where magneto acoustic tags are excited by a magnetic field and the corresponding mechanical resonance is then detected (see, e.g., U.S. Pat. No. 5,565,847).

An extrapolation of this technology is to monitor the acoustic or electromagnetic signal produced by a resonating magneto elastic sensor to determine an environmental condition. For example, it is well known that the resonant frequency of a magneto elastic material varies with temperature. It is also well known that applying a mass changing, moisture sensitive coating to a magneto elastic material causes the resonant frequency to vary with relative humidity. Various conventional sensor systems are based in significant part on these noted principles.

By utilizing selective coatings that vary according to a desired condition or conditions, other environmental conditions can also be determined. Illustrative are the pH sensors disclosed in C. A. Grimes, *A Remotely Interrogatable Magnetochemical pH Sensor*, IEEE Transactions on Magnetics 33:5(1997), pp. 3412-3414.

A significant challenge still, however, exists in incorporating a suitable sensor into the often limited space provided by existing pharmaceutical packaging. Indeed, most pharmaceutical packaging, such as an individual blister in a blister pack, have extremely limited internal space.

For example, in Jain, et al., *Magnetoacoustic Remote Query Temperature and Humidity Sensors*, Smart Mater. Struck. 9(2000), pp. 502-510 a 12 mm by 24 mm magneto acoustic sensor is disclosed. In U.S. Pat. Nos. 6,359,444, 6,393,921 and 6,397,661, Grimes, et al. similarly disclose magneto acoustic sensors having dimensions that range from 5 mm×37 mm to 10 mm×20 mm.

As is well known in the art, the noted sensors are too large for placement in blister packs and other conventional pharmaceutical packaging. Moreover, such sensors cannot be easily reduced in size, since size reduction substantially changes the resonant and interrogation frequencies, as well as the amplitude of the generated signal. Further, the mass changing, moisture sensitive materials disclosed by Jain et al. would yield unsatisfactory results since they would not exhibit enough mass change when employed in conjunction with a smaller sensor (i.e., magneto elastic strip).

It is therefore an object of the present invention to provide a highly efficient, cost effective means for sensing and/or monitoring environmental conditions and determining values relating thereto within a multitude of pharmaceutical packaging and, in particular, pharmaceutical packaging having limited internal space.

It is another object of the present invention to provide a remote query magneto elastic sensor system and method for sensing and/or monitoring at least one, preferably, a plurality of environmental conditions and determining at least one value relating thereto within pharmaceutical packaging.

It is another object of the present invention to provide a remote sensor system and method for sensing temperature within pharmaceutical packaging.

It is another object of the present invention to provide a remote sensor system and method for sensing the relative or percent humidity within pharmaceutical packaging.

SUMMARY OF THE INVENTION

In accordance with the above objects and those that will be mentioned and will become apparent below, the present invention relates to systems and methods for remotely sensing or monitoring environmental conditions and determining values relating thereto within pharmaceutical packaging, such as a blister pack. In one embodiment of the invention, the invention comprises a sensor assembly configured to be disposed within the interior of the packaging (e.g., blister). The assembly comprises a holder (or housing) having a sensor disposed therein. Preferably, the holder includes a substantially micro porous section configured to communicate the environmental conditions inside the packaging to the interior of the holder.

The sensors of the invention preferably comprise a magneto elastic alloy in the form of a strip. In one embodiment, the sensors comprise an iron-based amorphous, metallic glass alloy. Preferably, the sensors have a length in the range of 3-5 mm and a width in the range of 1-2 mm. The sensors have a magneto-elastic resonant frequency that varies according to a given environmental condition, whereby determining the resonant frequency allows the environmental condition to be calculated.

In a further embodiment, the invention comprises a packaging assembly wherein the sensor is secured to a portion of the packaging material itself. In one aspect of the invention, the sensor is directly attached to the lid of a blister pack wherein the sensor is disposed proximate a blister when the lid is subsequently sealable bonded to the base. In a further aspect, the sensor is attached to the base, preferably, within a blister.

In another embodiment, the invention comprises a packaging assembly wherein the sensor is disposed proximate the lid in a cantilevered configuration.

In a further aspect, the sensor includes a moisture sensitive coating that preferably changes mass in response to a change in relative humidity. In a further embodiment, more than one sensor is employed to facilitate simultaneous sensing of a plurality of environmental conditions and determination of values relating thereto.

In yet another embodiment of the invention, the packaging assembly of the invention includes an interrogation coil, a receiver and a memory, wherein the receiver is configured to detect acoustical energy radiated by the sensor in response to energy impulses from the interrogation coil and the memory is configured to record signals communicated from the transducer. By employing the data stored in the memory, it can be determined whether the interior of the pharmaceutical packaging experienced temperature or humidity extremes that might degrade the quality of the pharmaceutical composition contained therein. In a further aspect, the packaging assembly includes a processor that is adapted to analyze the data in the memory and determine at least one environmental condition value (e.g., ° C.), and a display to convey pertinent data and information to a user.

The invention also comprises methods for remotely sensing environmental conditions and determining values relating thereto within pharmaceutical packaging. Such methods include the steps of placing at least a first sensor having a magneto elastic resonant frequency inside the packaging, applying a magnetic pulse (i.e., interrogation pulse) to the first sensor, measuring the acoustic response of the first sensor, processing the measured acoustic response to determine the resonant frequency of in first sensor, and determining at least a first environmental condition within the packaging based upon the resonant frequency of the first sensor. Preferably, the environmental condition being sensed or monitored comprises temperature or relative humidity. In a further embodiment, a second sensor is also placed inside the packaging to determine a second environmental condition.

Determination of the resonant frequency of the sensor preferably includes making a reference measurement of acoustic response of the packaging material without a sensor present. The acoustic response of the sensor can then be processed in light of the reference measurement by subtracting the reference signal from the acoustic signal generated by the sensor.

BRIEF DESCRIPTION OF THE DRAWINGS

Further features and advantages will become apparent from the following and more particular description of the preferred embodiments of the invention, as illustrated in the accompanying drawing, and in which like referenced characters generally refer to the same parts or elements throughout the views, and in which:

FIG. 1 is a top plan view of a prior art blister strip;

FIG. 2 is a perspective view of a prior art blister strip;

FIG. 3 is a top plan view of a prior art blister pack;

DETAILED DESCRIPTION OF THE PREFERRED EMBODIMENT

Figure 4:
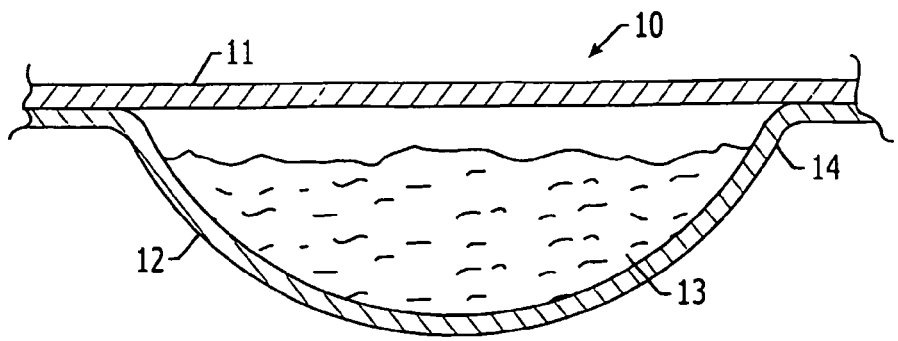
FIG. 4 a partial section view of a prior art blister containing a pharmaceutical composition.

Before describing the present invention in detail, it is to be understood that this invention is not limited to particularly exemplified systems or process parameters as such may, of course, vary. It is also to be understood that the terminology used herein is for the purpose of describing particular embodiments of the invention only, and is not intended to limit the scope of the invention in any manner.

All publications, patents and patent applications cited herein, whether supra or infra, are hereby incorporated by reference in their entirety to the same extent as if each individual publication, patent or patent application was specifically and individually indicated to be incorporated by reference.

It must be noted that, as used in this specification and the appended claims, the singular forms "a," "an" and "the" include plural referents unless the content clearly dictates otherwise. Thus, for example, reference to "a blister" includes two or more such blisters.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In describing the present invention, the following terms will be employed, and are intended to be defined as indicated below.

Definitions By the terms "magneto elastic element" and "sensor element", as used herein, it is meant to mean and include a component, element or strip comprising a material (or a component, element or strip having a portion of a material) that exhibits a magneto elastic resonant frequency in response to a magnetic stimulus including, but not limited to, materials referred to as soft magnetic and magnetostrictive materials, and, in particular, the Metglas™ materials available from Allied Signal Corporation.

By the term "medicament", as used herein, is meant to mean and include any substance (i.e., compound or composition of matter) which, when administered to an organism (human or animal) induces a desired pharmacologic and/or physiologic effect by local and/or systemic action. The term therefore encompasses substances traditionally regarded as actives, drugs and bioactive agents, as well as biopharmaceuticals (e.g., peptides, hormones, nucleic acids, gene constructs, etc.) typically employed to treat diseases and inflammatory and respiratory disorders (e.g., asthma), including, but not limited to, analgesics, e.g., codeine, dihydromorphine, ergotamine, fontanel or morphine; angina preparations, e.g., diltiazem; antiallergics, e.g., cromoglycate (e.g., as the sodium salt), ketotifen or nedocromil (e.g., as the sodium salt); anti-infective e.g., cephalosporins, penicillin's, streptomycin, sulphonamides, tetracycline's and pentamidine; antihistamines, e.g., methapyrilene; anti-inflammatory, e.g., beclomethasone (e.g., as the dipropionate ester), fluticasone (e.g., as the propionate ester), flunisolide, budesonide, rofleponide, mometasone (e.g., as the furcated ester), ciclesonide, triamcinolone (e.g., as the actinide), 6α,9α-dilutor-11β-hydroxyl-16α-methyl-3-ox-17α-propionyloxy-androsta-1,4-dyne-17β-carbothioic acid S-(2-oxo-tetrahydro-furan-3-yl) ester or 6α,9α-dilutor-17α-[(2-furanylcarbonyl)oxy]-11β-hydroxyl-16α-methyl-3-oxoandrosta-1,4-dyne-17β-carbothioic acid S-Fluor methyl ester; antitussives, e.g., mescaline; bronchodilators, e.g., ablution (e.g., as free base or soleplate), salmeterol (e.g., as inflate), ephedrine, adrenaline, fenoterol (e.g., as hydro bromide), formatter (e.g., as fumigate), Isoprinosine, metaproterenol, phenylephrine, phenylpropanolamine, pirbuterol (e.g., as acetate), reporter (e.g., as hydrochloride), rimier, terbutaline (e.g., as sulphatc), isoetharine, tulobuterol or 4-hydroxyl-7-[2-[[2-[[3-(2-henylethoxy)propyl]sulfonyl]ethyl]amino]ethyl-2(3H)-benzothiazolone; PDE4 inhibitors e.g. colonialist or roflumilast; leukotriene antagonists e.g. montelukast, pranlukast and zafirlukast; adenosine 2a agonists, e.g., (2R,3R,4S,5R)-2-[6-Amino-2-(1S-hydroxymethyl-2-phenyl-ethylamine)-purring-9-yl]-5-(2-ethyl-2H-terrazzo-5-yl)-tetra hydro-furan-3,4-idol (e.g., as male ate); $\alpha_4$ integrant inhibitors, e.g., (2S)-3-[4-({[4-(amino carbonyl)-1-piperidinyl]carbonyl}oxy)phenyl]-2-[((2S)-4-methyl-2-{[2-(2-methylphenoxy)acetyl]amino}pentane)amino]propane acid (e.g., as free acid or potassium salt)], diuretics, e.g., amyloidal; anticholinergics, e.g., ipratropium (e.g., as bromide), tiotropium, atropine or oxitropium; ganglion stimulants, e.g., nicotine; hormones, e.g., cortisone, hydrocortisone or prednisolone; xanthenes, e.g., aminophylline, chorine theophyllinate, lysine theophyllinate or theophylline; therapeutic proteins and peptides, e.g., insulin or glucagon; vaccines, diagnostics, and gene therapies. The noted medicaments may be employed in the form of salts, (e.g., as alkali metal or amine salts or as acid addition salts) or as esters (e.g., lower alkyl esters) or as solvates (e.g., hydrates) to optimize the activity and/or stability of the medicament.

The term "medicament" specifically includes ablution, salmeterol, fluticasone propionate and beclomethasone dipropionate and salts or solvates thereof, e.g., the soleplate of ablution and the inflate of salmeterol.

The term "medicament" further includes formulations containing combinations of active ingredients, including, but not limited to, salbutamol (e.g., as the free base or the sulfate salt) or salmeterol (e.g., as the inflate salt) or formatter (e.g., as the fumigate salt) in combination with an anti-inflammatory steroid such as a beclomethasone ester (e.g., the dipropionate), a fluticasone ester (e.g., the propionate), a furcated ester or budesonide.

By the terms "medicament formulation" and "pharmaceutical composition", as used herein, it is meant to mean a combination of at least one medicament and one or more added components or elements, such as an "excipient" or "carrier." As will be appreciated by one having ordinary skill in the art, the terms "excipient" and "carrier" generally refer to substantially inert materials that are nontoxic and do not interact with other components of the composition in a deleterious manner. Examples of normally employed "excipients," include pharmaceutical grades of carbohydrates, including monosaccharide's, disaccharides, cyclodextrins and polysaccharides (e.g., dextrose, sucrose, lactose, raffinose, manifold, orbital, instill, dextrins and maltodextrins); starch; cellulose; salts (e.g., sodium or calcium phosphates, calcium sulfate, magnesium sulfate); citric acid; tartaric acid; lysine; leonine; high molecular weight polyethylene glycols (PEG); plutonic; surfactants; lubricants; separates and their salts or esters (e.g., magnesium separate); amino acids; fatty acids; and combinations thereof.

The noted medicaments and recipients may be prepared as composite materials, such as by co-precipitation or by coating, or other method known in the art, or may be prepared from batches of separately prepared individual particles which are subsequently blended together to form particulate mixtures of medicament and recipient particles.

By the term "pharmaceutical delivery device", as used herein, it is meant to mean a device that is adapted to administer a controlled amount of a composition to a patient, including, but not limited to, the Diskus® device disclosed in U.S. Pat. Nos. Des. 342,994, 5,590,654, 5,860,419, 5,837,630 and 6,032,666. The term "pharmaceutical delivery device" further includes the Diskhaler™ device disclosed in U.S. Pat. Nos. Des. 299,066; 4,627,432 and 4,811,731; the Rotahaler™ device disclosed in U.S. Pat. No. 4,778,054; the Cyclohaler™ device by Norvartis; the Turbohaler™ device by Astra Zeneca; the Twisthaler™ device by Schering Plough; the Handihaler™ device by Boehringer Ingelheim; the Airmax™ device by Baker-Norton; and the Dura and Inhaled Therapeutic active delivery systems. Each of the noted "pharmaceutical delivery devices" are incorporated by reference herein.

By the terms "pharmaceutical packaging" and "packaging", as used herein, it is meant to mean conventional pharmaceutical containment systems and packaging having at least one sealable pocket, cavity or blister adapted to contain at least one medicament or a pharmaceutical composition in any conventional form, including a powder, capsule or tablet. The terms "pharmaceutical packaging" and "packaging" thus include conventional blister strips, disks (e.g., Rotadisk™), packs, sheets and individual containers that are employed in the aforementioned "pharmaceutical delivery devices", including, but not limited to, the pharmaceutical packaging disclosed in U.S. Pat. Nos. 6,032,666, 6,155,423 and 4,778,054.

As will be appreciated by one having ordinary skill in the art, the present invention substantially reduces or eliminates the disadvantages and drawbacks associated with conventional sensor systems and methods for monitoring environmental conditions. As discussed in detail below, the sensors of the invention can readily be disposed proximate to or in one or more blisters of a blister strip pack, disk or sheet to determine temperature and moisture profiles proximate a pharmaceutical composition sealed therein. The sensors of the invention can also be readily disposed or incorporated in a multitude of containment structures or individual containers, such as a vial.

Referring first to FIGS. 1 and 2, there is shown conventional pharmaceutical packaging in the form of a blister strip 10. As illustrated in FIGS. 1 and 4, the blister strip 10 includes a lid 11 and a base 14 having a plurality of blisters 12 formed therein adapted to receive a pharmaceutical composition 13, preferably in the form of a dry powder. Each blister 12 typically has a length in the range of 1.5 to 8.0 mm and a width in the range of 1.5 to 8.0 mm. More typically, the width is approximately 4.0 mm.

Referring now to FIG. 3, there is shown further prior art pharmaceutical packaging in the form of a blister pack 16. The blister pack 16 similarly includes a lid (not shown) and a base 17 having a plurality of blisters 18 formed therein adapted to receive a pharmaceutical composition 13.

As indicated, the sensors of the invention preferably comprise a component, element or strip comprising a material, or a component, element or strip having a portion of a material, having a magneto elastic resonant frequency. The sensors can thus be remotely monitored by application of an interrogating magnetic pulse and subsequent reception and interpretation of the acoustic signal generated by the sensors.

Preferably, the sensors of the invention comprise a magneto elastic alloy, including, but not limited to, iron, cobalt, samarium, yttrium, gadolinium, terbium and dysprosium. More preferably, the sensors comprise an iron based, amorphous metallic glass alloy, such as the Metglas™ materials available from Allied Signal Corp. Even more preferably, the sensors comprise Metglas™ 2826.

In a preferred embodiment of the invention, the sensors have a length in the range of approximately 3-5 mm, more preferably, 2.5-4.5 mm, a width in the range of approximately 1-2 mm, and a thickness in the range of approximately 1-100 µm, more preferably, 1-10 µm. Even more preferably, the sensors have a length of approximately 4 mm, a width of approximately 1.5 mm and a thickness of approximately 2 µm.

The sensors of the invention have a resonant frequency in the range of 100 kHz -1 MHz, more preferably, in the range of 300 kHz -700 kHz. Even more preferably, the sensors of the invention have a resonant frequency in the range of 500 kHz -600 kHz.

According to the invention, the sensors can be constructed using known manufacturing processes. Preferably, the sensors, i.e., magneto elastic ribbons, are produced by rapid melt quenching under vacuum. As is known in the art, continuously depositing a suitable metal alloy on a wheel causes one side of the resulting ribbon to have a relatively smooth side and a relatively rough side. As is also well known in the art, these characteristics augment the acoustic wave generated by the oscillation of the sensor at its resonant frequency.

Since the resonant frequency of a sensor depends upon its physical shape and size, accurate determinations of environmental conditions without calibration require precisely controlled formation of the sensor, particularly, when employing a plurality of sensors. Each sensor must thus be very uniform. Accordingly, in a preferred embodiment of the invention, the sensors are cut to a predetermined size and shape via laser cutting that is controlled by a computer (CNC) or a template.

As will be appreciated by one having ordinary skill in the art, the sensors of the invention can be monitored without direct physical connections or specific orientation requirements. According to well established principles, the magneto elastic sensors (or elements) generate elastic energy in response to an AC magnetic field interrogation field. The elastic energy deforms the sensor, causing vibration at the resonant frequency of the sensor. Such vibrations generate an acoustic wave that can be detected remotely using a suitable receiver, such as an electro acoustic transducer. The response of a magneto elastic sensor is thus independent of the relative orientation of the interrogation field, although it is preferred to have the magnetic vector aligned.

According to the invention, at least one frequency in the range of approximately 1-100 kHz, more preferably, 20-40 kHz is employed to interrogate the magneto acoustic sensors of the invention. Even more preferably, the interrogation frequency is matched to the physical size of the sensor. Thus, for example, a suitable frequency for interrogating a 4×1.5 mm sensor is approximately 30 kHz. Since the sensors are preferably sized and configured for use within pharmaceutical packaging and, hence, are quite small, the corresponding interrogation frequency is generally relatively high (e.g., 400-1000 kHz).

In an additional embodiment of the invention, a time-varying interrogation frequency in the range of 20 Hz-1 GHz is employed to interrogate the sensors. Preferably, the time-varying frequency ranges from approximately $0.85 \times \phi$ to $1.25 \times \phi$, where $\phi$ represents the magneto-elastic resonant frequency of a respective sensor, and the time ranges from 0-10 min.

According to the invention, detecting (or determining) the resonant frequency generated by the magneto acoustic sensor facilitates the determination of (i) changes in the environmental condition(s) being sensed or monitored (e.g., temperature or humidity) and/or (ii) values relating to the environmental condition(s). As is well known in the art, the resonant frequency of a magneto elastic sensor is proportional to the Young's modulus of the material. It is also known that Young's modulus is proportional to temperature. Employing this well established principle, one can determine the temperature proximate the sensor and changes thereto by determining the resonant frequency of the sensor. Further, applying a moisture sensitive coating to the sensor, such that the mass of the sensor changes with variations in relative humidity, likewise alters the resonant frequency of the sensor, facilitating assessment of the moisture content or humidity proximate the sensor.

Similarly, any chemispecific coating exhibiting mass change characteristics in the presence of an analyze may be used to assess other environmental conditions such as pH or the concentration, presence or absence of specific substances. Accordingly, in additional embodiments of the invention, a plurality of sensors are employed to facilitate simultaneous sensing and/or monitoring of a plurality of environmental conditions and the determination of values relating thereto.

According to the invention, coatings particularly suitable for the practice of this invention include any moisture sensitive materials and/or compounds that change mass in response to changes in humidity, including, but not limited to, metallic oxides, such as aluminum or titanium oxides, and polymers, including polysilsesquioxanes, such as 1,4-phenyl-bridged polysilsesquioxane [1,4-Bis(triethoxysilyl)benzene]. In a preferred embodiment of the invention, the coating comprises 1,4-phenyl-bridged polysilsesquioxane, which exhibits a surface area of approximately 958 $m^2/g$.

Due to the relatively small size of sensors, the noted coatings offer significant surface loading. Preferably, the surface area of the coatings is greater than approximately 450 $m^2/g$ and a preferred range is approximately 450-1350 $m^2/g$.

According to the invention, the coating thickness can be tailored to produce desired performance characteristics. Generally, applying a thicker coating increases the potential surface area, which increases the mass change for a given change in humidity. However, a thicker coating also dampens the resonant frequency of the sensor, decreasing the available signal.

Various conventional methods can be employed to coat the sensors, including chemical vapor deposition, sol gel, sputtering, dip coating and spin coating. Preferably, the sensors of the invention are coated via sequentially dip coating (e.g., 4-8 cycles) and bake dried in a vacuum oven.

Preferably, the coating thickness is in the range of approximately 0.001-50 μm. More preferably, the coating thickness is in the range of approximately 0.001-30 μm. Even more preferably, the coating thickness is in the range of approximately 0.005-10 μm.

According to the invention, the coating need not cover the entire sensor(s), but rather, cover only that portion of the sensor(s) necessary to produce a desired acoustic response when subject to a magnetic pulse.

Figure 5:
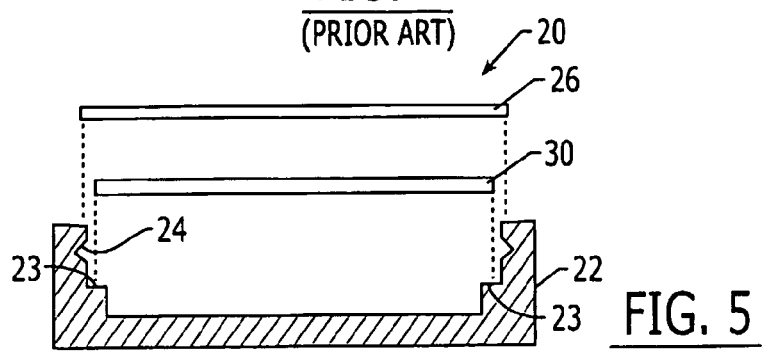
FIG. 5 is a partial section, exploded view of one embodiment of a sensor assembly, according to the invention.
Figure 6A:
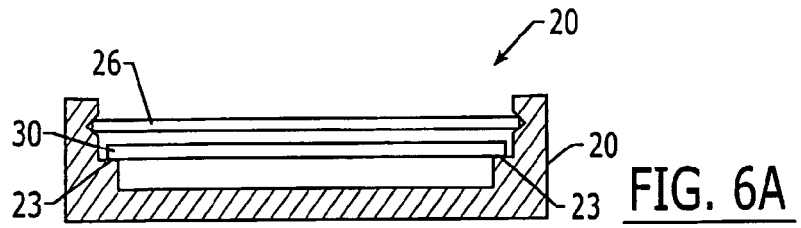
FIG. 6A is a partial section, assembled view of the sensor assembly shown in FIG. 5, according to the invention.
Figure 7:
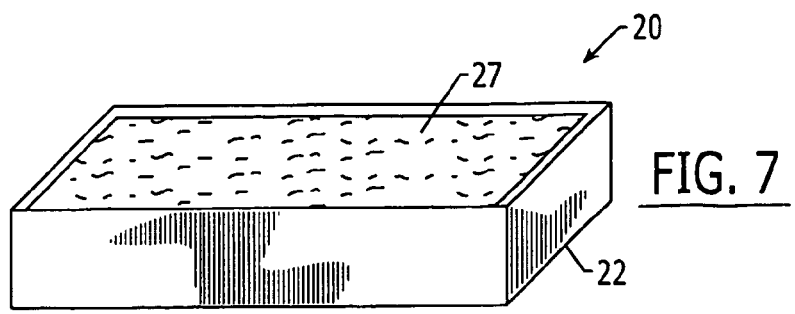
FIG. 7 is a perspective view of the sensor assembly shown in FIG. 6A, according to the invention.

Referring now to FIGS. 5, 6A and 7, there is shown one embodiment of the sensor assembly 20 of the invention. As illustrated in FIG. 5, the sensor assembly 20 includes a housing or holder 22, a sensor 30 and a lid 26. The holder 22 preferably includes a sensor seat 23 or other conventional means adapted to receive and position the sensor 30 within the holder 22 such that the sensor 30 is free to move or oscillate when disposed thereon (see FIG. 6A). The holder 22 further includes a lid engagement portion 24 preferably adapted to facilitate a snap fit of the lid 26 to the holder 22, as illustrated in FIG. 6A. As will be appreciated by one having ordinary skill in the art, the lid 26 can also be bonded to the holder 22 via a conventional adhesive.

Figure 6B:
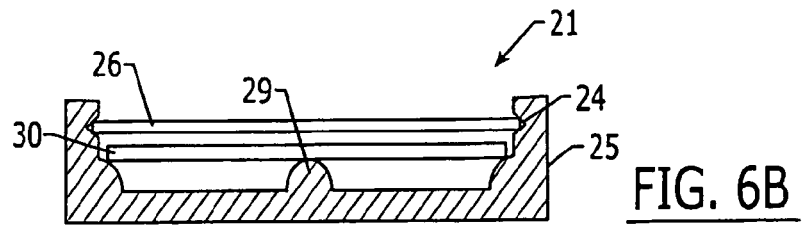
FIG. 6B is a partial section, assembled view of a further embodiment of a sensor assembly, according to the invention.

Referring now to FIG. 6B, there is shown a further embodiment of a sensor assembly 21. In this embodiment, the holder 25 includes a sensor support 29 that is positioned and adapted to support the sensor 30 proximate the center portion thereof. The sensor 30 is thus similarly free to oscillate when positioned on the sensor support 29.

As will be appreciated by one having ordinary skill in the art, various additional, substantially non-restrictive means may be employed to receive and position the sensor 30 in the housing 22, 25 of the invention. Such means includes the placement of additional sensor supports 29 proximate the ends of the sensor 30.

According to the invention, the holders 22, 25 can be constructed out of various non-metallic (e.g., polymeric) materials, such as polyvinyl chloride (PVC), high density polyethylene (HDPE), Nylon™ and Teflon™. In a preferred embodiment, the holders 22, 25 are constructed of a low viscosity polymer (e.g., SL 5510™).

As will be appreciated by one having ordinary skill in the art, the holders 22, 25 of the invention can comprise various sizes and shapes to accommodate a multitude of applications. In one embodiment of the invention, the holder 22 has a maximum length in the range of 1.6-5.6 mm, a maximum width in the range of 2-8 mm, and a maximum height (with the lid 26 secured thereon) in the range of approximately 0.5-2.5.

Referring now to FIG. 7, the lid 26 preferably includes a substantially microporous section 27 to facilitate the ingress of moisture into the holder 22. Preferably, the microporous section 27 comprises a plurality of pores having an average diameter in the range of 5-10 μm. As will be appreciated by one having ordinary skill in the art, the noted pore size is sufficient to allow the ingress of moisture while restricting the ingress of the pharmaceutical composition into the holder 22.

Preferably, the lid 26 is similarly constructed of a non-metallic material. In a preferred embodiment, the lid 26 is constructed out of a low viscosity polymer, such as SL 5510™.

Figure 8:
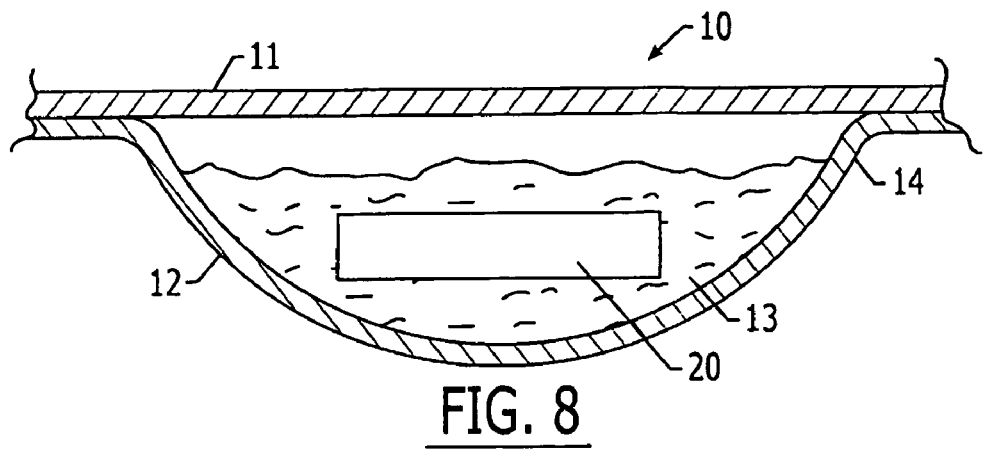
FIG. 8 is a partial section view of a blister containing a sensor assembly, according to the invention.

Referring now to FIG. 8, in one embodiment of the invention, the sensor assembly 20 is disposed in a blister (or pocket) 12. In accordance with a further embodiment of the invention, one additional sensor assembly 20 is disposed in a second blister 12. As discussed herein, the noted arrangement facilitates substantially simultaneous and/or sequential assessment of multiple environmental conditions.

According to the invention, the sensor assembly 20 (or assemblies) is preferably disposed in the blister(s) prior to filling the blister(s) with a pharmaceutical composition. Alternatively, a two-step fill operation can be employed wherein the blister(s) are pre-filled to a first level, the sensor assembly 20 positioned therein and post-filled to the desired dosage level.

Figure 9:
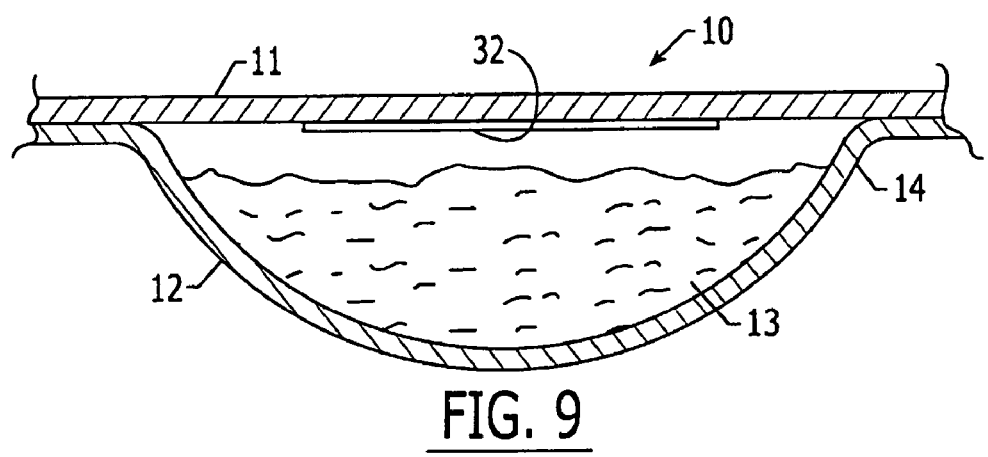
FIG. 9 is a partial section view of one embodiment of a sensor packaging assembly, according to the invention.

Referring now to FIG. 9, there is shown a further embodiment of the invention. In the noted "packaging assembly" embodiment, at least one sensor 32 is preferably attached (on one end thereof) to the lid 11 of the pharmaceutical packaging or blister pack 10 prior to sealable bonding the lid 11 to the base 14. Since only one end of the sensor 32 is secured to the lid 11, the sensor 32 is free to oscillate at its resonant frequency in response to an interrogation pulse.

As illustrated in FIG. 9, the sensor 32 is preferably positioned on the lid 11 such that after bonding the lid 11 to the base 14, the sensor 32 is disposed proximate, preferably, immediately above, the blister 12. In additional envisioned embodiments of the invention, not shown, the sensor 32 is suitably attached to the base 14 proximate to or within a respective blister 12.

Figure 10:
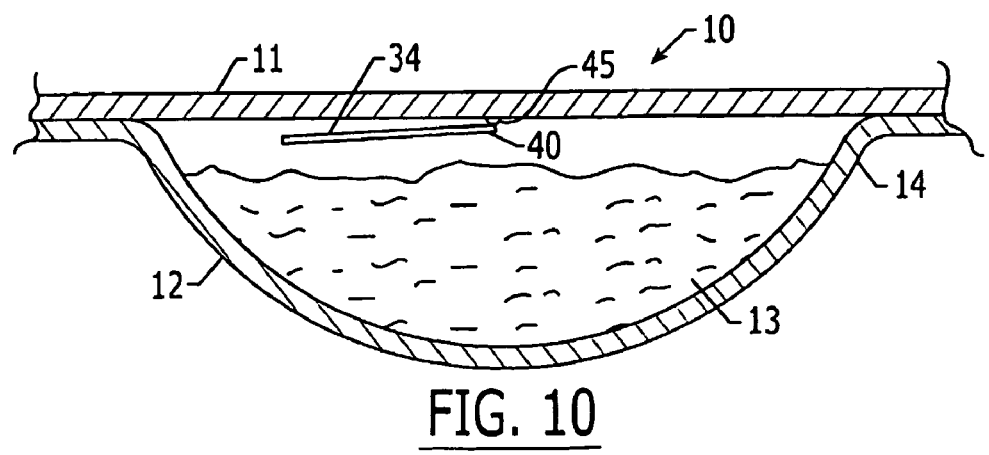
FIG. 10 is a partial section view of a further embodiment of a sensor packaging assembly, according to the invention.

Yet another embodiment of the invention is shown in FIG. 10, wherein the packaging assembly 40 similarly comprises a lid 11 with at least one sensor 34 disposed thereon. According to the invention, a support 45 suspends the sensor 34 on the lid 11 in a cantilever configuration to permit an acoustic response. Preferably, the support 45 is formed as an integral portion of the lid 11 and, hence, blister strip 10.

Figure 11:
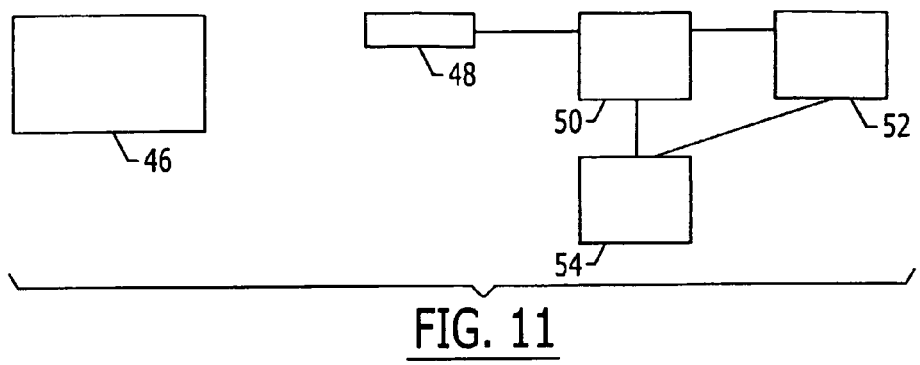
FIG. 11 is a schematic illustration of a further embodiment of a sensor packaging assembly, according to the invention.

As shown schematically in FIG. 11, in a preferred embodiment, the packaging assembly 40 further includes an interrogation coil 46, a receiver 48, a processor 50, a memory 52 and a display 54. As will be appreciated by one having ordinary skill in the art, the interrogation coil 46, receiver 48, processor 50, memory 52 and display 54, described below, can similarly be incorporated into the above described sensor assemblies 20, 21 shown in FIGS. 5-7 and the packaging assembly embodiment shown in FIG. 9 and, hence, is deemed a further aspect of the invention.

According to the invention, at least one AC magnetic pulse (or interrogation pulse) is applied by interrogation coil 46, which generates an oscillation in sensor 34 at its resonant frequency. This oscillation in turn generates an acoustic signal (or signals) that can be detected by a high gain, low noise antenna receiver 48. Preferably, the receiver 48 detects a plurality of the acoustic signals (or values thereof) of the sensor over the preferred range (or ranges) of successive (or time-varying) interrogation frequencies. The processor 50 then determines the resonant frequency and calculates an environmental condition based on that resonant frequency. Memory 52 is adapted to store at least the data detected and communicated by the receiver 48 as well as the calculated environmental conditions calculated and communicated by the processor 50.

Preferably, the results generated by the processor 50, data and information stored in memory 52 and other pertinent information is visually displayed on display 54. During operation, the noted system would readily allow a user to determine whether the pharmaceutical packaging and, hence, pharmaceutical composition disposed therein, had experienced temperature or humidity levels that would effect the efficacy of the pharmaceutical composition.

In these latter embodiments, it is important the packaging material be oriented such that a minimum amount of the pharmaceutical composition disposed therein is in contact with the sensor (e.g., 32, 34) during interrogation, so that the resonant frequency is not altered or muted.

Figure 12:
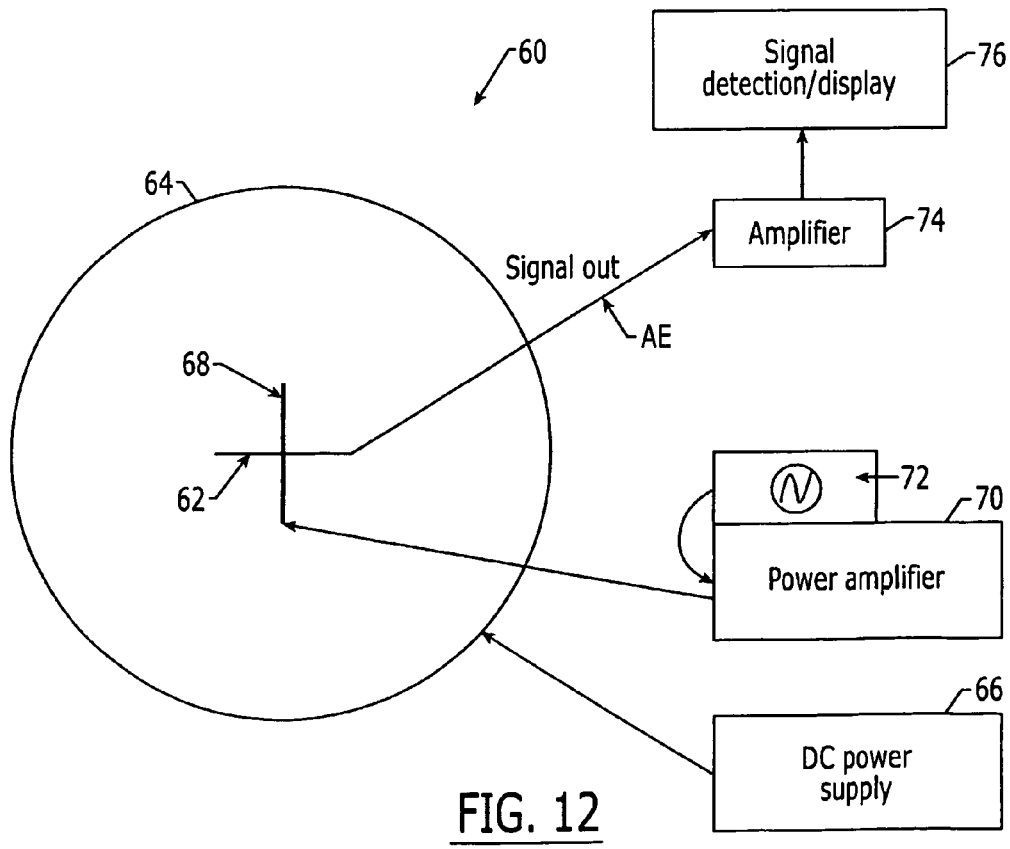
FIG. 12 is a schematic illustration of one embodiment of a sensor system, according to the invention.

Referring now to FIG. 12, there is shown a schematic representation of one embodiment of a sensor system 60 of the invention. According to the invention, a sensor 62 is disposed proximate a biasing DC coil 64, powered by power supply 66. The system 60 further includes an AC interrogation coil 68, which is fed by power amplifier 70 and frequency generator 72. In response to the interrogation field, sensor 62 generates acoustic energy (denoted generally by Arrow AE) that is received by amplifier 74 and visually displayed on display 76.

The DC biasing field is preferably oriented along the length of the sensor 62 and has an amplitude configured to optimize the acoustic response of the sensor 62. Preferably, the amplitude of the DC field is automatically selected by a processor by polling the sensor 62 with different amplitudes to determine the maximum acoustic response. The DC field can alternatively be produced by a magnetically-hard material.

In a further embodiment of the invention, now shown, the DC biasing field is eliminated. Although generally deemed required in most magneto acoustic based systems, Applicant has found that acceptable acoustic responses can be generated and assessed without the DC biasing field.

Figure 13:
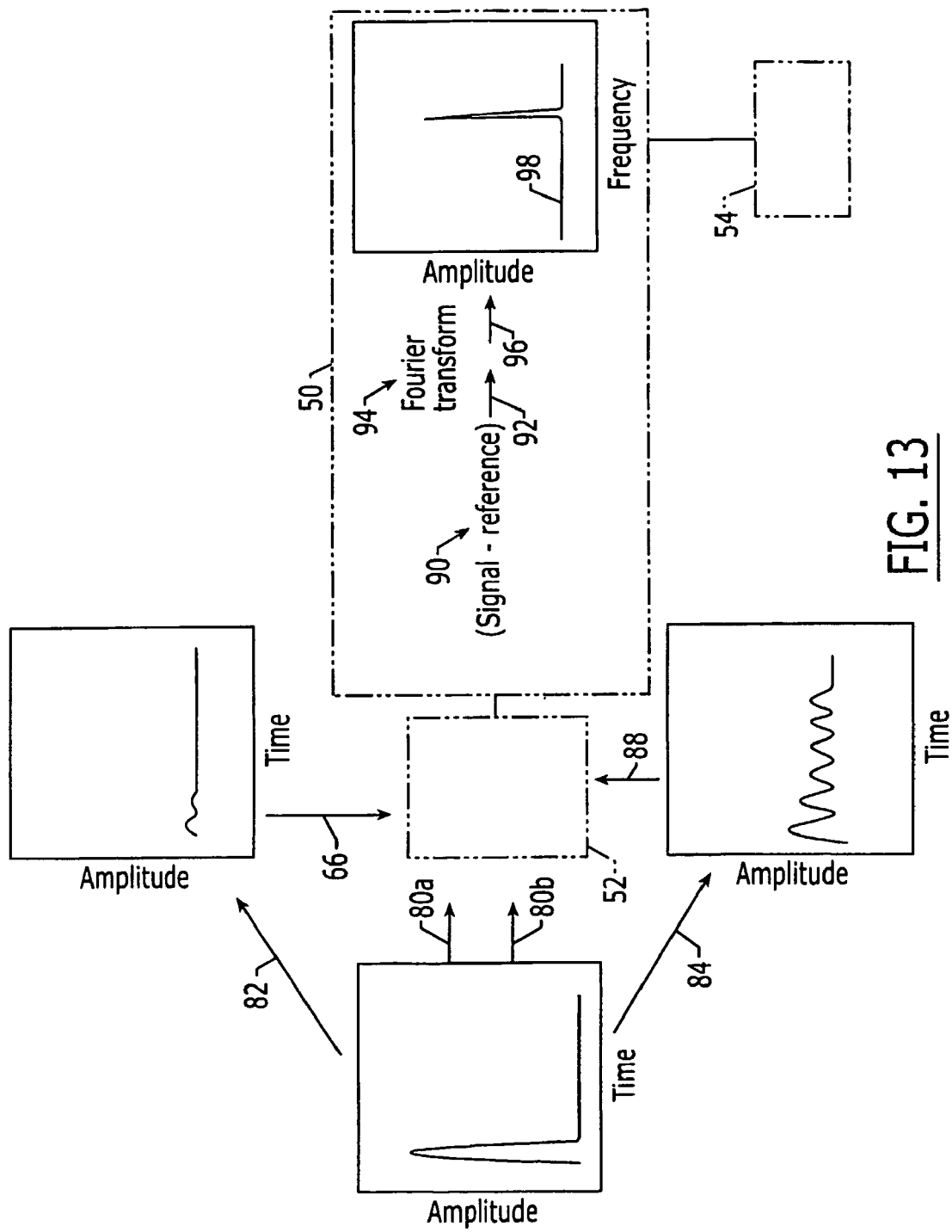
FIG. 13 is a flow chart illustrating one embodiment of the signal processing performed by the systems and methods of the invention.

Referring now to FIG. 13, there is shown a flow chart representing one embodiment of the signal processing performed by the systems and methods of the invention. As will be appreciated by one having ordinary skill in the art, given the relatively high frequency interrogation pulse made necessary by the small size of the sensors of the invention, it is important to minimize background noise. Accordingly, in a preferred embodiment, at least a first AC interrogation pulse 80a is applied to the pharmaceutical packaging "without" a sensor (or sensors). In response to the first AC pulse 80a, the packaging generates a reference signal 82. The reference signal 82 is then detected by the receiver, recorded 86 and stored in memory 52.

A second, substantially similar AC interrogation signal is then applied to the pharmaceutical packaging with a sensor disposed thereon, as illustrated in FIGS. 9 and 10, or contained therein, as illustrated in FIG. 8. The acoustic signal produced by the sensor(s), corresponding to the resonant frequency thereof, is then similarly detected and recorded in memory 52.

According to the invention, the processor 50 subtracts the reference signal 82 (or value corresponding thereto) from the acoustic signal 84 (denoted 90) (or value corresponding thereto) to produce a first, substantially clean signal 92. Indeed, applicant has found that the noted technique substantially reduces, and in many instances, eliminates the background noise that is often associated with magneto acoustic techniques.

As illustrated in FIG. 13, the processor 50 further performs a Fourier transformation 94, preferably, a fast Fourier transform (FFT) of signal 92 to determine the "true" sensor resonant frequency 98.

The resonant frequency 98 is then employed to determine an environmental condition value, such as temperature (e.g., ° C.) or percent humidity. As indicated above, the environmental condition value(s), ambient environmental conditions, etc., can then be selectively displayed on the display 54 of the invention.

In an additional embodiment of the invention, the noted signal processing includes a "pre-sampling" step. According to the invention, the pre-sampling step comprises applying one or more AC interrogation pulses to the sensor prior to determining the desired environmental condition from the resonant frequency. Applicant has found that the pre-sampling step further minimizes the artifacts that are often encountered in monitoring electronics.

Accordingly, in one embodiment of the invention, the signal processing comprises (i) determining a reference frequency (or reference signal value), as described above, (ii) pre-correlating a series of "pre-sampled" resonant frequency values to determine a first resonant frequency, (iii) determining a second resonant frequency by subtracting the reference frequency from the first resonant frequency, and (iv) determining at least one environmental condition value using the second resonant frequency.

Figure 14:
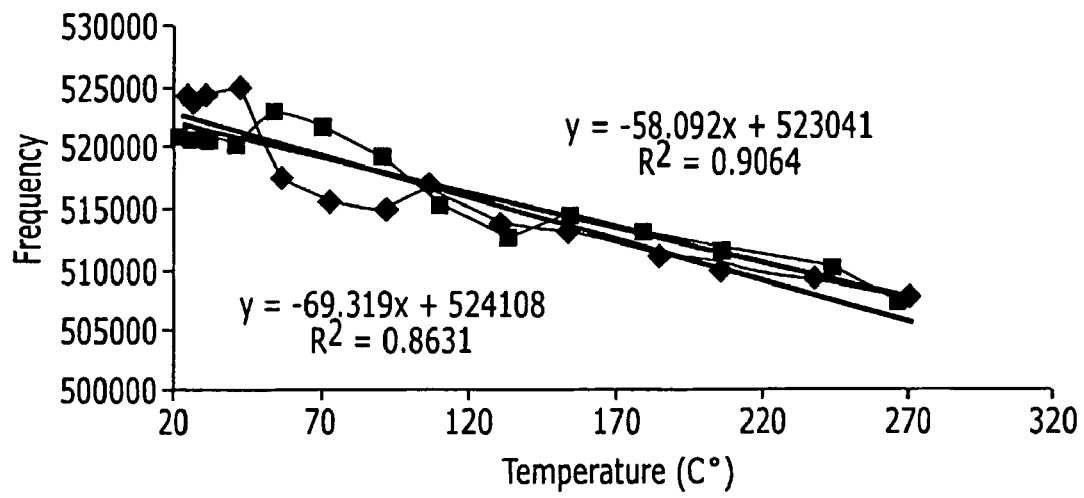
FIG. 14 is a graph illustrating the proportional relationship between resonant frequency and temperature for a sensor of the invention.

Referring now to FIG. 14, there is shown a graph illustrating the proportional relationship between temperature and measured resonance frequency of a sensor (i.e., magneto acoustic strip) contained within a blister pack 10, such as that illustrated in FIG. 1. As illustrated in FIG. 14, the resonant frequency of the sensor is substantially proportional to the Young's modulus of the material. There is also a linear decrease in the Young's modulus with increased temperature for amorphous metallic glasses, which is in accord with prior art teachings.

EXAMPLES

The following examples illustrate the systems and methods of the invention. The examples are for illustrative purposes only and are not meant to limit the scope of the invention in any way.

Example 1

Three magneto acoustic strips comprising Metglass™ 2826 having a length of approx. 5.5 mm, a width of approx. 1.5 mm and a thickness of approx. 2 μm were initially prepared. The strips were then coated with 1,4-phenyl-bridged polysilsesquioxane (PBP). The coating and drying process for each strip is set forth in Table I.

TABLE I

| Strip | Coating Process | Drying Process |
| --- | --- | --- |
| Strip 1 | PBP coating dropped on* | Air dried for ~4 hrs |
| Strip 2 | PBP coating sequentially applied four (4) times via dip coating | Bake dried in a vacuum oven for ~4 hrs. |
| Strip 3 | PBP coating sequentially applied eight (8) times via dip coating | Bake dried in a vacuum oven for ~4 hrs. |

*By the term "dropped on" it is meant to mean direct deposition (e.g., eye dropper deposition)

Each of the strips were then placed in a humidity chamber and subjected to a range of relative humidity, during which the resonant frequency was recorded.

Figure 15:
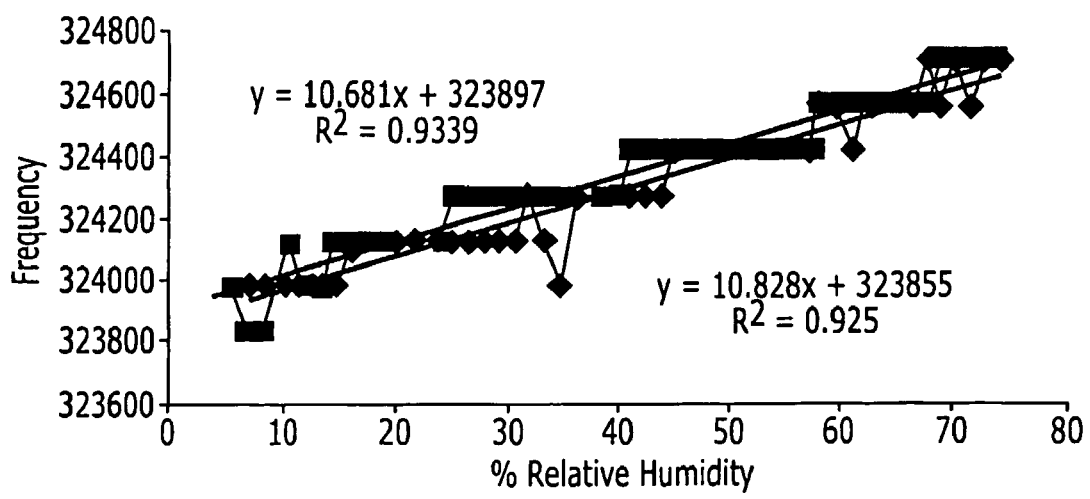
FIGS. 15 through 18 are graphs reflecting the detected resonant frequencies of coated sensors over a range of relative humidity.

Referring first to FIG. 15, there is shown the results achieved for Strip 1. The results reflect a substantially linear relationship between the resonant frequency and relative humidity.

Figure 16A:
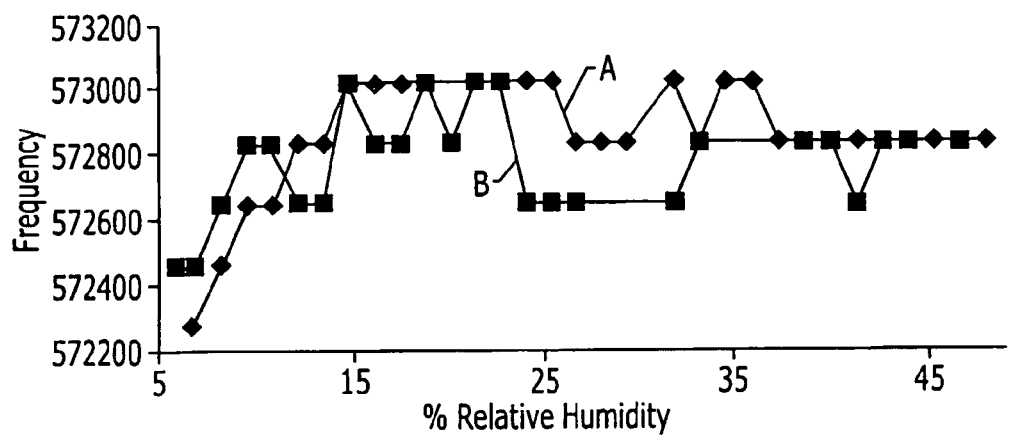
Figure 16B:
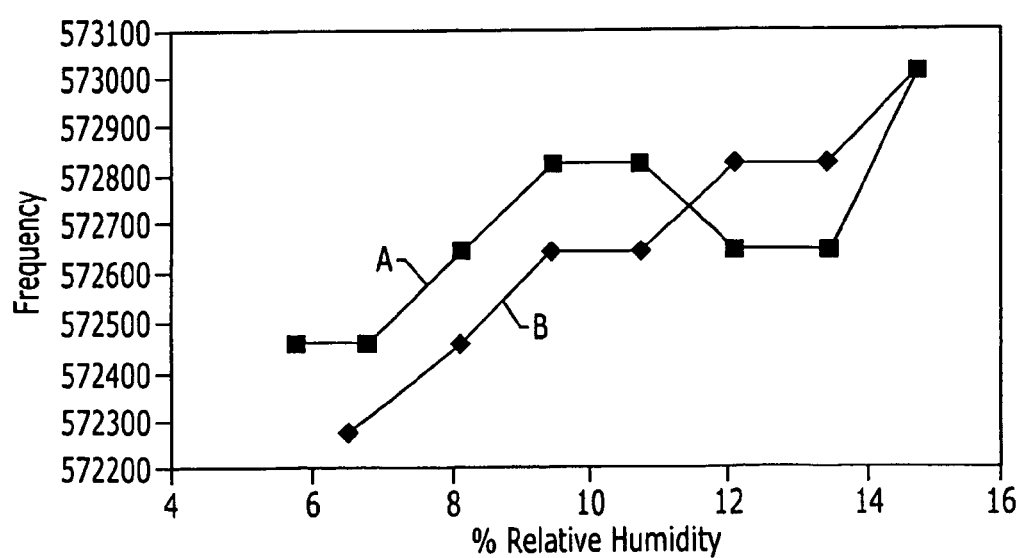
Figure 17:
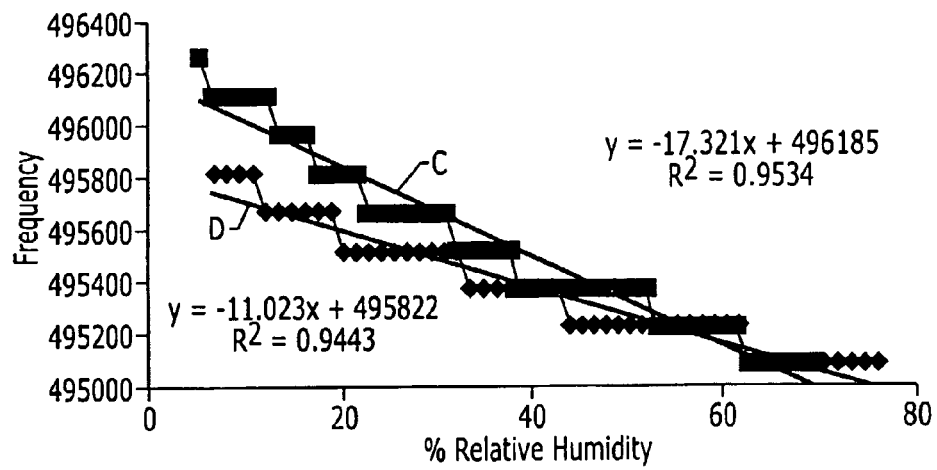
Figure 18:
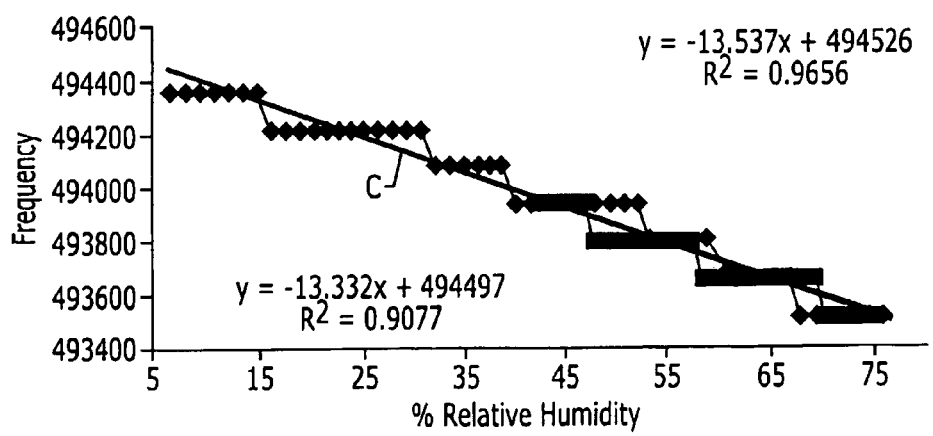

Referring now to FIGS. 16A and 16B, there is shown the results achieved for two (2) samples (A, B) of Strip 2. As illustrated in FIG. 16B, a linear relationship between the resonant frequency and relative humidity was initially reflected (i.e., ~5-15%), which became random at relative humidity >15%, as shown in FIG. 16A. However, when the strips were coated eight (8) times, a substantially linear relationship was reflected with two samples (C, D) over a broad range of relative humidity (see FIG. 17). The results were also substantially consistent (i.e., reproducible) during successive runs (see FIG. 18).

Without departing from the spirit and scope of this invention, one of ordinary skill can make various changes and modifications to the invention to adapt it to various usages and conditions. In particular, the invention has been described primarily in reference to the determination of temperature and humidity within pharmaceutical packaging. However, the invention may be applied to remotely determine any suitable environmental condition within any package, container or other enclosed space. As such, these changes and modifications are properly, equitably, and intended to be, within the full range of equivalence of the following claims.

What is claimed is:

1. A packaging assembly for sensing an environmental condition within pharmaceutical packaging, comprising:
   a base sheet having at least one pocket formed therein and being adapted such that a pharmaceutical composition is contained therein, wherein said pharmaceutical composition is an inhalable dry powder composition;
   a lid sheet, said lid sheet including a pocket portion, said pocket portion being disposed proximate said pocket and wherein said lid sheet is bonded to said base sheet to form a sealed blister pack; and
   a sensor element comprising a material that is responsive to said environmental condition and having a magnetoelastic resonant frequency in the range of 300-700 kHz, said sensor element generating at least a first acoustic signal at said resonant frequency in response to an AC magnetic pulse, said sensor element being present within said sealed blister pack and attached to said pocket portion of said lid sheet within said pocket and configured to measure environmental conditions within said said sealed blister pack.

2. The packaging assembly of claim 1, wherein said sensor element includes first and second ends.

3. The packaging assembly of claim 2, wherein said first end of said sensor element is attached to said lid sheet pocket portion.

4. The packaging assembly of claim 1, wherein said sensor element includes a support adapted to engage said lid sheet pocket portion.

5. The packaging assembly of claim 4, wherein said first end of said sensor element is secured to said support whereby said second end of said sensor element is cantilevered.

6. The packaging assembly of claim 1, wherein said assembly includes an interrogation coil adapted to provide said AC magnetic pulse to said sensor element to generate said first acoustic signal.

7. The packaging assembly of claim 1, wherein said assembly further includes a receiver adapted to detect said first acoustic signal.

8. The packaging assembly of claim 1, wherein said sensor element comprises a magnetoelastic alloy.

9. The packaging assembly of claim 8, wherein said magnetoelastic alloy comprises a material selected from the group consisting of iron, cobalt, samarium, yttrium, gadolinium, terbium and dysprosium.

10. The packaging assembly of claim 8, wherein said magnetoelastic alloy comprises an iron based, amorphous metallic glass alloy.

11. The packaging assembly of claim 10, wherein said iron based, amorphous metallic glass alloy comprises Metglass™ 2826.

12. The packaging assembly of claim 1, wherein said environmental condition comprises temperature.

13. The packaging assembly of claim 1, wherein said sensor element is coated with a moisture sensitive material.

14. The packaging assembly of claim 13, wherein said moisture sensitive material exhibits a change in mass in response to a change in a second environmental condition.

15. The packaging assembly of claim 14, wherein said second environmental conditions comprises humidity.

16. The packaging assembly of claim 13, wherein said moisture sensitive material comprises 1,4-phenyl-bridged polysilsesquioxane.

17. The packaging assembly of claim 1, wherein said packaging assembly further includes a memory adapted to receive and store at least said first acoustic signal, a processor for determining at least a first environmental condition value using said first acoustic signal, and a display.

* * * * *

UNITED STATES PATENT AND TRADEMARK OFFICE
CERTIFICATE OF CORRECTION

PATENT NO. : 7,429,127 B2  Page 1 of 1
APPLICATION NO. : 10/512268
DATED : September 30, 2008
INVENTOR(S) : Dwight Sherod Walker and Michael Bernard James It is certified that error appears in the above-identified patent and that said Letters Patent is hereby corrected as shown below:

On the Cover page, After (65) Prior Publication Data section, please insert

-- Related U.S. Application Data
Provisional application No. 60/375,522, filed on April 25, 2002 --

Signed and Sealed this

Tenth Day of February, 2009

JOHN DOLL
*Acting Director of the United States Patent and Trademark Office*